United States Patent [19]

Narayanan et al.

[11] Patent Number: 5,206,386
[45] Date of Patent: Apr. 27, 1993

[54] CONTROLLED RELEASE N-SUBSTITUTED PYRROLIDONE ESTERS AND PROCESS FOR THE USE THEREOF

[75] Inventors: Kolazi S. Narayanan, Palisades Park; Paul D. Taylor, West Milford, both of N.J.

[73] Assignee: ISP Investments Inc., Wilmington, Del.

[21] Appl. No.: 675,367

[22] Filed: Mar. 20, 1991

[51] Int. Cl.$^5$ .................. C07D 207/27; A61K 31/40
[52] U.S. Cl. .................................. 548/551; 548/413
[58] Field of Search .................. 548/551, 413; 514/91, 514/424

[56] References Cited

U.S. PATENT DOCUMENTS 4,162,325 7/1979 Rodriquez et al. .................. 548/551

FOREIGN PATENT DOCUMENTS 0241050 10/1987 European Pat. Off. ............ 548/551
0040458 2/1989 Japan .................................... 548/551

Primary Examiner—David B. Springer
Attorney, Agent, or Firm—Jules E. Goldberg; Joshua J. Ward

[57] ABSTRACT

N-substituted cyclic lactam esters are made from biologically active organic acids and N-haloalkyl substituted cyclic lactam, preferably N-chloromethyl pyrrolidone. Such esters provide slow release of the organic acids in situ through slow hydrolysis of the ester to release the organic acid and the N-alkyl substituted cyclic lactam. The esters are useable for delivering a large variety of biologically active organic acids in slow release fashion to target organisms and promote effective long term therapeutic treatment. In particular, an ester made from acetyl salicyclic acid and chloromethyl pyrrolidone provides a vehicle for dermal penetration and slow release of aspirin for long term treatment.

4 Claims, No Drawings

CONTROLLED RELEASE N-SUBSTITUTED PYRROLIDONE ESTERS AND PROCESS FOR THE USE THEREOF

TECHNICAL FIELD

This invention relates to novel controlled release N-substituted cyclic lactam esters and more particularly to N-substituted pyrrolidone esters and to a method for the manufacture thereof using haloalkylpyrrolidone.

BACKGROUND OF THE INVENTION

Percutaneous drug delivery has attracted much interest in the field of local and systemic chemotherapy. However, most drugs themselves cannot penetrate the skin at high enough rates for therapeutic efficiency. Various approaches have been attempted to deliver drugs across the skin and additionally release the drug in a controlled fashion.

It is also desirable to develop a delivery system for delivering biologically active agents such as drugs, herbicides, fungicides, insecticides, etc. to target organisms, by oral, dermal, parenteral or foliar administration, with the agents still subject to controlled release. However, no satisfactory system has yet been developed, and the search continues for delivery compounds which are easily manufactured and have increased penetration rates for carrying drugs or other biologically active agents to a delivery site, with effective controlled release of the drug or agent through slow and controllable hydrolysis.

SUMMARY OF THE INVENTION

It is an object of the present invention to provide novel N-substituted cyclic lactam esters which are usable as carriers for various biologically active agents.

It is another object to provide novel N-substituted pyrrolidone esters which are usable as carriers for various biologically active agents.

It is a further object to provide N-substituted cyclic lactam or pyrrolidone esters which are easily manufactured for delivering various biologically active acids to specific sites which are then released slowly from the N-substituted cyclic lactam or pyrrolidone moiety by hydrolysis.

It is a further object to provide a method for producing novel N-substituted pyrrolidone esters of biologically active acids using chloromethylpyrrolidone.

These and other objects of the present invention are achieved by providing N-substituted cyclic lactam esters of the following formula I:

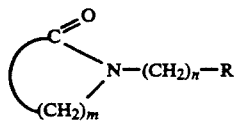

where n=1 to 3 and m=3, 4 or 5 and R is an organic acid moiety of a biologically active carboxylic, phosphoric, phosphonic, sulfonic group or thiocyanate which hydrolyses to release the acid group.

More particularly, N-substituted pyrrolidone esters of the following formula II may be used:

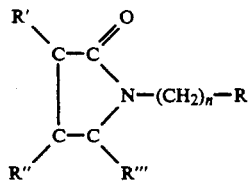

where R', R" and R'" are lower alkyl, alkoxy, cycloalkyl, aralkyl or H, at least one of R', R" or R'" being H; n=1 or 2 and where R is an organic moiety of a biologically active carboxylic, phosphoric, phosphonic, sulfonic group or thiocyanate which hydrolyses to release the acid group. Preferably, R', R" and R'" are hydrogen and R is a carboxylic acid having a chloromethyl, bromomethyl, phenyl, or substituted phenyl functional moiety, such as acetyl salicylate, among others.

Most particularly, N-substituted pyrrolidone esters of the following Formula III may be used:

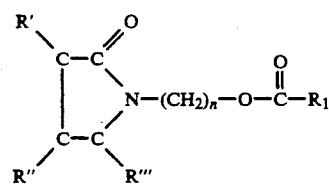

where R', R" and R'" are lower alkyl, alkoxy, cycloalkyl, aralkyl or H, at least one of R', R" or R'" being H; n=1 or 2 and where $R_1$ is an organic moiety derived from acids from the group consisting essentially of aspirin (acetyl salicylic acid), 2,4 dichlorophenoxy acetic acid, 3,6, dichloro 2- methoxybenzoic acid, endothall, clauvanic acid, nicotinic acid, alpha and beta naphthoic acids, N-phenylphthalamic acid, p-toluene sulfonic acid, phenylphosphonic acid, hexanoic acid, acrylic acid, glycine, alpha-amino butyric acid, phosphonomethyl glycine, amiben, indobufen, indoprofen, indomethacin, ibuprofen, clavulanic acid and amoxycillin.

For the purposes of this disclosure, the terms "cyclic lactam" and "pyrrolidone" are used interchangeably, and such use does not limit the scope of the invention.

One method for producing the novel N-substituted pyrrolidone esters of Formulas I-III comprises reacting a biologically active organic acid with an amine of low nucleophobicity to provide an ammonium salt of the acid, and reacting the ammonium salt of the acid with N-haloalkyl substituted pyrrolidone to provide an N-substituted pyrrolidone ester. Preferably, N-chloromethylpyrrolidone is used.

The biologically active acid moiety replaces the halo group in the pyrrolidone compound and is thus carried by the N-substituted pyrrolidone to a target site where hydrolysis deposits the resultant acid in a slow controlled fashion. Other examples of functional groups which may be carried and deposited in this fashion include thiocyanates. Preferably the esters are prepared in an appropriate solvent i.e. methylene chloride, prior to purification, or are formulated directly in a solvent such as N-methyl pyrrolidone.

Alternatively a solution or suspension of the acid salt, such as sodium thiocyanate, dissolved in a suitable solvent, such as N-methylpyrrolidone, is reacted with the haloalkylpyrrolidone. The two reactants react almost immediately to form an insoluble by-product salt, such as sodium halide and the product ester, N-pyrrolidonylmethyl thiocyanate. The product ester remains dissolved in the solvent with the insoluble salt easily separated, for example, by filtration. This provides a ready to use product ester solution in N-methylpyrrolidone.

DETAILED DESCRIPTION OF THE INVENTION

The present invention preferably utilizes the reaction of a biologically active organic acid with an amine of low nucleophobicity to produce an ammonium salt of the acid. The ammonium salt of the acid so produced is then reacted with N-haloalkyl substituted cyclic lactam to produce compounds of the formula I:

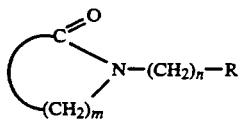   I where n=1 to 3 and m=3, 4 or 5 and R is an organic moiety of a biologically active carboxylic, phosphoric, phosphonic, sulfonic group or thiocyanate which hydrolyses to release the acid.

More particularly, N-substituted pyrrolidone esters of the Formula II are produced:

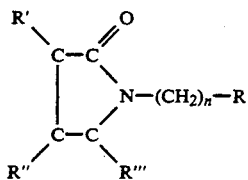   II where R', R" and R'" are lower alkyl, alkoxy, cycloalkyl, aralkyl or H, at least one of R', R" or R'" being H; n=1 or 2 and where R is an organic moiety of a biologically active carboxylic, phosphoric, phosphonic, sulfonic or thiocyanate group which hydrolyses to release an acid. Preferably, R', R" and R'" are hydrogen and R is a carboxylic acid having a chloromethyl, bromomethyl, phenyl, or substituted phenyl functional moiety, such as acetyl salicylate, among others.

Most particularly, N-substituted pyrrolidone esters of Formula III may be used:

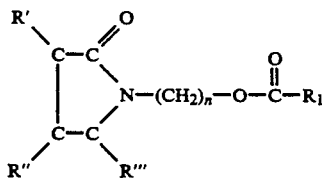   III where R', R" and R'" are lower alkyl, alkoxy, cycloalkyl, aralkyl or H, at least one of R', R" or R'" being H; n=1 or 2 and where $R_1$ is an organic moiety derived from acids from the group consisting essentially of aspirin(acetyl salicylic acid), 2,4 dichlorophenoxy acetic acid, 3,6 dichloro, 2- methoxybenzoic acid, endothall, clauvanic acid, nicotinic acid, alpha and beta naphthoic acids, N-phenylphthalamic acid, p-toluene sulfonic acid, phenylphosphonic acid, hexanoic acid, acrylic acid, glycine, acid, phosphonomethyl glycine, amiben, indobufen, indoprofen, indomethacin, ibuprofen, clavulanic acid and amoxycillin.

The preferred reaction is illustrated as follows:

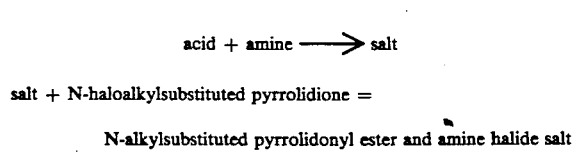

salt + N-haloalkylsubstituted pyrrolidione =

N-alkylsubstituted pyrrolidonyl ester and amine halide salt

This is preferred as standard esterification methods using hydroxymethylpyrrolidone and a biologically active acid, such as aromatic carboxylic acid catalyzed by a mineral acid, produce electrophilic substituted products, not esters. For example, reacting benzoic acid and hydroxymethylpyrrolidone produces o-,p-substituted N-pyrrolidonylmethyl benzoic acid.

Numerous acids could be reacted in this fashion to provide novel esters from N-halosubstituted cyclic lactam. Once made, the organic acid is reformed by hydrolysis in a controlled fashion, slowly releasing the biologically active organic acid when contacted with water, the rate controllable by adjusting pH. For example, an ester of benzoic acid, comprising N-benzoyloxymethyl-2-pyrrolidone or N-(2-pyrrolidonyl)methyl benzoate, has increased water solubility, enhanced bioavailability and dermal penetration, yet undergoes slow hydrolysis, to release N-hydroxymethyl- pyrrolidone and benzoic acid.

The method of the present invention has the advantage of producing N-pyrrolidonyl esters of high purity and at conditions which prevent degradation of the organic acid, thus preventing a reduction in therapeutic effectiveness. Such esters also increase biological activity by their increased capacity for dermal penetration.

Among the organic acids or salts usable for preparing esters of the present invention are β-napthoic acid, nicotinic acid, p-toluene sulfonic acid, phenyl phosphonic acid, hexanoic acid, acrylic acid, glycine, alpha-aminobutyric acid, phosphonomethylglycine, 3,6 dichloro-2-methoxybenzoic acid, endothall, amiben, acetyl salicylic acid, indobufen, indoprofen, indomethacin, ibuprofen, clavulanic acid and amoxycillin. Of course, various other biologically active organic acids could be used in the present invention.

Compounds usable as the N-halosubstituted cyclic lactam include but are not limited to chloromethyl pyrrolidone, N-chloromethyl-2-pyrrolidone, N-chloroethyl-2-pyrrolidone, N-chloromethyl caprolactum, N-chloromethyl valerolactum, or 4-carbalkoxy derivatives of these compounds, and other N-substituted pyrrolidonyl alkyl halides.

The compounds of this invention are most preferably prepared from stoichimetric amounts of N-chloromethylpyrrolidone and the diisopropylethyl ammonium salt of the subject acid in a suitable solvent such as methylene chloride. The diisopropylethyl ammonium salt of the acid may be prepared in situ by the addition of a stoichiometric quantity of diisopropylethyl amine to a solution of the acid in methylene chloride or by the addition of the ammonium salt, made separately from the amine and acid, to a solution of N-chloromethylpyrrolidone. The following is representative of this method:

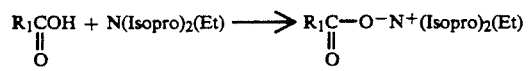

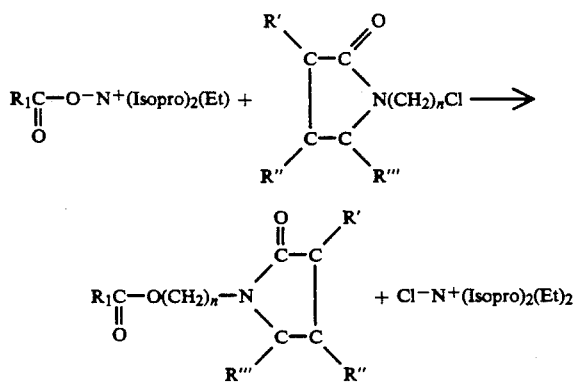

Alternatively, the following method may be used:

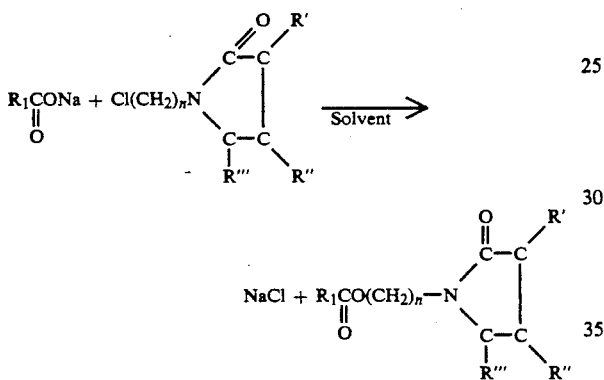

Any other amine may be used, provided the ammonium salt of the organic acid is soluble in the solvent and the amine does not undergo nucleophilic substitution reaction with chloromethylpyrrolidone. Among the amines usable with the present invention are tertiary amines, such as triethyl amine or tributyl amine.

If subject acid salts are available which provide the necessary properties for reaction, these may be used directly to produce the novel esters. Alkali metal salts of the subject acids may be used instead of the ammonium salts. However, a suitable solvent other than methylene chloride should be used as the metal salts of the acids are typically insoluble in methylene chloride. N-methylpyrrolidone is a preferred solvent when using the alkali metal salts.

Toluene and acetonitrile may be used as solvents in the preparation of the present esters from both ammonium salts and metal salts. However, the yields may be lower and the products less pure than when using methylene chloride, and it is more difficult to recover the product ester from these solvents.

The N-pyrrolidonylmethyl esters of carboxylic acids of Formula III are preferred as they are more water soluble than conventional esters produced from aliphatic, cycloaliphatic or aromatic alcohols, and are expected to have increased dermal penetration. With conventional esters, the rate of hydrolytic release of the carried acid compound is inadequate, and thus the present compounds have better bioavailability.

The inventive esters hydrolyze slowly in the presence of water to yield the parent organic acid or salt from which they were made, and N-hydroxymethylpyrrolidone. For example, N-pyrrolidonylmethylbenzoate hydrolyses slowly to deposit benzoic acid, slowly releasing the biologically active organic acid in situ, to provide long acting biological activity. The N-hydroxymethylpyrrolidone metabolite has low toxicity ($LD^{50}$ 5000 mg/KG) and biodegrades without causing adverse effects. Pyrrolidones are known to be transdermally absorbed and the esters enjoy the same propensity for absorption, providing a vehicle for delivering biologically active acids transdermally, with the rate of acid deposition controlled by the rate of hydrolysis.

The pyrrolidonylmethyl esters could be synthesized in an aprotic solvent, recovered and introduced into a mammal, plant or insect by oral, dermal or parenteral and foliar administration. Aqueous body fluids would hydrolyze the esters slowly, thereby releasing the biologically active acid. In other in-vivo systems, the rate of acid released could be controlled by adjusting the pH to control the time effectiveness of the active acid.

The following is a partial list of acids convertible to N-substituted pyrrolidonyl esters:

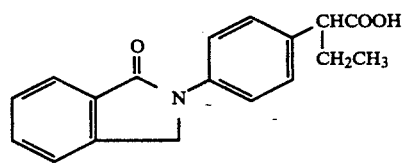

indobufen

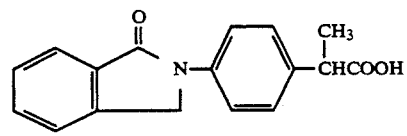

indoprofen

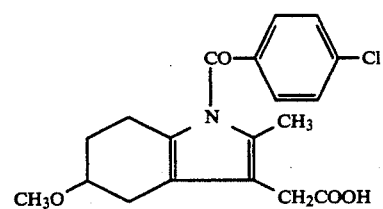

indomethacin

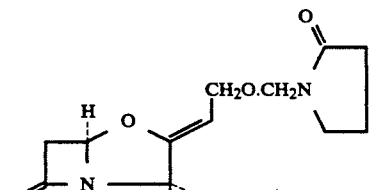

[Pat. No. 4,215,128]

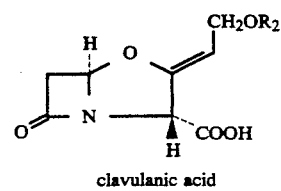

clavulanic acid

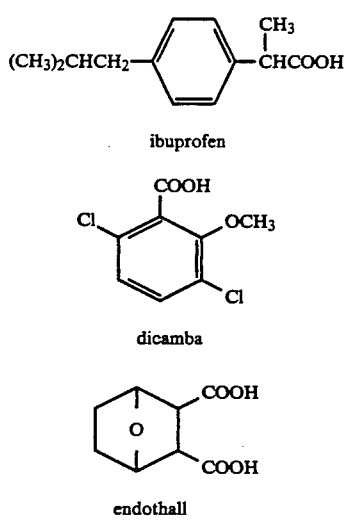

ibuprofen dicamba endothall

EXAMPLE 1

The preparation of N-chloroacetoxymethyl-2-pyrrolidone.

A four-necked 500 ml round bottom flask fitted with a magnetic stirrer, condenser, thermometer, and a nitrogen gas inlet and dropping funnel was charged with 9.5 grams (0.1 mole) of chloroacetic acid dissolved in 200 ml of methylene dichloride. The mixture was cooled in a water bath while 15.5 grams of diisopropylethyl amine (0.12 moles) was dropped in slowly over a period of ten minutes. A solution of 13.4 grams of N-chloromethyl-pyrrolidone (0.1 mole) dissolved in 50 ml of methylene dichloride was added slowly over a period of about 1 hour, the mixture stirred thereafter for six hours and left to stand over night under a nitrogen blanket.

The mixture was then washed twice with 200 ml portions of water and the resultant organic layer dried over magnesium sulfate and filtered. The filtrate was stripped of solvent in a rotary evaporator.

A light yellow oil residue weighing 14 grams and having a boiling point 110°–111° C. (0.1 mm Hg) Was recovered with evidence of slight decomposition. The yield was 73% and the compound had a refractive index No. at 25° C. equal to 1.4905. Infrared, Hlnmr and $^{13}$C nmr spectra were consistent with the structure of N-chloroacetoxymethyl-2 pyrollidone

EXAMPLE 2

Preparation of N-bromoacetoxymethyl-2-pyrollidone.

The same procedure was followed as that followed in Example except that 13.9 grams of bromoacetic acid (0.1 mole) dissolved in 120 ml of methylene dichloride were used instead of 9.5 grams of chloroacetic acid. Instead of standing overnight, the reaction mixture was heated and maintained at a reflux temperature for 3 hours and then, after cooling, worked up as described in Example 1. The light yellow oil residue weighed 12.12 grams for a yield of 51.4% and had a refractive index of 1.4930°. IR, H$^1$nmr and $^{13}$C nmr spectra were consistent With the structure N-bromoacetoxymethyl-2 pyrrolidone.

EXAMPLE 3

The preparation of N-benzoyloxymethyl-2 pyrrolidone.

The same procedure was followed as described in Example 1 except that 12.2 grams of benzoic acid dissolved in 180 ml of methylene dichloride was used instead of chloroacetic acid solution. Also, after standing overnight, the reaction mixture was heated at reflux for 8 hours, cooled and worked up as in Example 1. The liquid oil residue weighted 21 grams, for a yield of 96% and had a refractive index of 1.5415, with an IR, H$^1$nmr, $^{13}$C and mass spectra confirming the structure of N-benzoyloxymethyl-2 pyrrolidone.

To purify the product further, the oil was washed with 100 ml of water, dissolved in 100 ml of methylene dichloride, portioned twice with 100 ml of water, and the organic layer dried over magnesium sulfate and striped of solvent in a rotary evaporator. The oil solidified and the solid was recrystallized from toluene-petroleum ether in a 50/50 mixture. The solid melted at 50° C. and all spectra confirmed the structure.

An aqueous wash of the solvent, when left standing overnight, deposited fine crystals of pure benzoic acid. This indicated that the N-pyrrolidonylmethyl esters hydrolyze slowly in the presence of water, to slowly release the acid moiety.

EXAMPLE 4

Preparation of N-(2-acetoxy)benzoyloxymethyl-2-pyrrolidone.

The same procedure is followed as described in Example 1, except that 18.6 9rams of aspirin (0.1 mole) is dissolved in 180 grams of methylene dichloride instead of chloroacetic acid solution. The solution is cooled in a water bath as 15.5 grams of diisopropylethyl amine (0.12 moles) is dropped in slowly over a period of ten minutes. After the addition, 13.4 grams of n-chloromethyl-2-pyrrolidone (0.1 moles), dissolved in 50 milliliters of methylene dichloride, is added slowly over a period of one hour. The reaction mixture is heated to reflux for eight hours, cooled and worked up as in Example 3. The liquid oil or solid product may be further purified by recrystallization.

The reactants are added in substantially a stoichiometric ratio between about 2:1 to 1:2, salt to N-haloalkylpyrrolidone. Preferably, the portion of reactants are in a 1:1 ratio, with up to a 20% excess of either of the ingredients preferred. The reaction temperatures are preferably at or near room temperature, though in some systems, the ingredients are preferably reacted at the solvent reflux temperature.

Numerous solvents could be used such as toluene, N-methyl pyrrolidone, methylene dichloride, acetonitrile or any solvent in which the reactants are soluble. However, hydroxylated solvents are believed to be unsatisfactory, since they could react with the reactant.

The reaction of the N-haloalkyl substituted pyrrolidone and a thiocyanate salt is carried out in N-methylpyrrolidone solvent as follows:

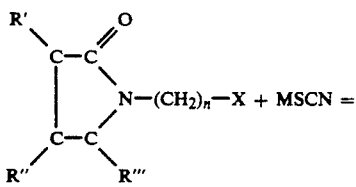

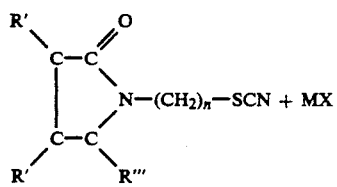

Where X is halide and M is sodium, potassium or ammonium.

Once in the N-methylpyrrolidone solvent, the reactants are mixed at a suitable temperature and for a sufficient period of time to complete the reaction with completion evidenced by the disappearance of one of the reactants. Thereafter, the reactant mixture is cooled and filtered to remove an alkali metal or ammonium salt which forms as a byproduct. The filtrate would typically contain a concentration of the thiocyanate in the range of 1 to 40 wt. %, preferably 10-30%, and most preferably 20-25%.

Conversions of the reactants to the product are in the range of about 90 to 95% based on the consumption of thiocyanate compound or formation of the byproduct metal halide. The filtrate may then be used as a preservative or biocide without further processing. Typically, however, additional compounds such as surface active agents, rheology modifiers, thickeners, or other adjuvants can be added to the filtrate to adjust properties.

The reaction can be carried out at temperatures of from 25° to 50° C. preferably 32° to 42° C. The reaction time depends on the choice of reactants as well as the reaction temperature but will typically range from 10 minutes to 24 hours, and preferably the reaction is carried out over 20 minutes to six hours.

A catalyst is not needed as the reaction proceeds fairly rapidly in N-methylpyrrolidone. The amount of N-methylpyrrolidone used is from 2-6 times the weight of the reactants and preferably 4-5 times the total reactant weight.

EXAMPLE 5

A three-necked 100 milliliter round bottom flask is fitted with a magnetic stirrer, thermometer, water condenser and nitrogen gas inlets and outlets to maintain a nitrogen atmosphere in the flask. The flask was charged with 8.38 grams (0.1035 moles) of sodium thiocyanate (NaSCN) dissolved in 50.7 grams of acetonitrile. The dropping funnel was charged with 12.92 grams of chloromethylpyrrolidone (0.0968 moles) which was added over a period of ten minutes to the flask, with constant stirring. During the addition, the temperature rose from 25° C. to 42° C. with the immediate formation a white precipitate. After about 30 minutes, the temperature stabilized at about 32° C. with the liquid in the flask turning a yellowish color.

The white precipitate was separated by filtration and found to be sodium chloride, having a weight of 5.6 grams (0.096 moles) evidencing an essentially complete reaction.

The yellow filtrate was collected and was tested using thin film chromatography using a 301-R Silica sheet and 10:90 methanol to dichloromethane solvent. The test showed two spots, at Rf equal to 0.30 and Rf equal 0.85. Gas liquid chromatography of the filtrate showed a major peak at 22.52 m whereas the starting material (N-chloromethylpyrrolidone) under identical conditions has a major peak at 17.18 m. Since N-chloromethylpyrrolidone is unstable under the conditions of chromatography, the results cannot be given a quantitative interpretation but do indicate that a new product was formed.

The filtrate was stripped of acetonitrile in a rotary evaporator leaving a residual oil. The oil was dissolved in methylene dichloride, washed twice with 50 ml of water and dried over magnesium sulfate. The dry residue was filtered, and the filtrate stripped of methylene dichloride. The resultant product was a crystalline solid melting at 52°-55° C., with decomposition (i.e. moisture was believed to be degrading the product). The product weight was 3.8 gm. Gas liquid chromatography of this material produced a major peak at 22.52 m and an IR spectrum showed two major peaks at 1692 cm-1 and 1247 cm-1.

EXAMPLE 6

The reaction disclosed in example 5 was repeated except that N-methyl pyrrolidone was used as the solvent, in place of acetonitrile.

A solution containing 0.537 gms. of N-chloromethylpyrrolidone dissolved in 5.0 gms. of N-methylpyrrolidone was stirred with the addition of 0.32 gms. of sodium thiocyanate at room temperature. A slight exotherm was observed. After 24 hours, a white precipitate formed and the mixture was filtered. The resulting solution showed a major peak at 22.55 m. Thus the isolated pure product obtained by synthesis in acetonitrile solvent was identical to that obtained in the N-methylpyrrolidone.

Without isolating the product, the filtrate showed the same retention time by gas liquid chromatography, and there was a quantitative recovery of sodium chloride, as before, indicating reaction completion. Judging from the recorded weight of NaCl the yield was about 90+% based on NaCl recovered discounting the loss from work up.

The biocidal activity of the N-(pyrrolidonyl) methyl thiocyanate was compared to the activity of methylene bisthiocyanate (MBT). A 10% solution of the pyrrolidone methyl thiocyanate of the Formula I where R=SCN, R', R'', and R''' are H and n=1, was prepared in N-methyl pyrrolidone. A 10% solution of MBT was similarly prepared. Both solutions were used to prepare test solutions by dilution, to provide samples having 150 ppm + or − of the active ingredient and tested against several bacterial antigens.

No growth was observed with streptococcus pyogenes organisms at 150 ppm, though other organisms tested up to 150 ppm were not controlled. This indicates some biocidal activity which may require further testing to determine optimum dosages for various organisms. The other organisms were staphylococcus aureus, escherichia coli, pseudomonas aeruginosa, aspergillus niger, chaetominum globosum, enterobacter aenogens, klebsiella pneumoniae, bacillus subtilis and clostridium sporogenies.

Utilizing N-methylpyrrolidone as the solvent during the production of N(pyrrolidonyl)alkyl thiocyanates eliminates the need for separation of the product thiocyanate from the solvent as the product is usable in the solution form. Thus a one step synthesis of a ready to apply material is produced.

Providing N-substituted cyclic lactam esters of organic acids provides products which are useable for the slow release of the biologically active organic acids in situ through slow hydrolysis. Such esters are easily made at relatively low temperatures which prevents the degradation of the organic acids and are made in sufficient high purity to allow use as slow release agents. Combined with the improved ability for transdermal penetration, such esters provide a unique vehicle for delivering biologically active acids for long term therapeutic treatment. While the present invention has been described in relation to particular reactant materials, it will be understood by those skilled in the art that various changes could be made in terms of temperature, time and reactant concentrations without varying from the scope of the present invention.

What is claimed is:

1. A controlled release N-alkylene substituted cyclic lactam ester of a biologically active organic acid as represented by Formula I:

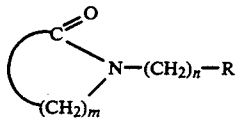

where $n=1$ to 3, $m=3$, and R is ester moiety of a biologically active medicinal carboxylic acid or amino carboxylic acid, the ester group being hydrolyzabel in vivo to release the biologically active carboxylic acid substance, where R is derived from a carboxylic acid from the group consisting of aspirin(acetyl salicyclic acid), 2,4 dichlorophenoxy acetic acid, 3,6, dichloro 2-methyoxybenzoic acid, endothall, alpha and beta naphthoic acids, N-phenylphthalamic acid, acrylic acid, glycine, alphaamino butyric acid, phosphonomethyl glycine, amiben, indobufen, idoprofen, indomethacin, and ibuprofen.

2. The ester of claim 1 where R is acetyl salicylate.

3. A controlled release N-alkylene substituted pyrrolidone ester of a biologically active acid as represented by Formula II:

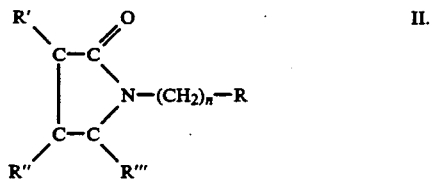

where R', R", and R'"are lower alkyl alkoxy, cycloalkyl, aralkyl or H, at least one of R', R" or '" being H; $n=1$ or 2 and where R is an organic moiety of a biologically active medicinal carboxylic acid or amino carboxylic acid, the ester hydrolyzable in vivo to release the biologically active carboxylic acid substance, where R is derived from a carboxylic acid from the group consisting of aspirin(acetyl salicyclic acid), 2,4 dichlorophenoxy acetic acid, 3,6 dichloro 2-methoxybenzoic acid, endothall, alpha and beta naphthoic acids, N-phenylphthalamic acid, acrylic acid, glycine, alphaamino butyric acid, phosphonomethyl glycine, amiben, indobufen, idoprofen, indomethacin, and ibuprofen.

4. A method for controllably releasing a biological active organic acid in situ comprising:
providing the N-alkylene substituted cyclic lactam ester of the biologically active organic acid of claim 1;
contacting the ester with aqueous body fluids, and,
hydrolyzing the ester in vivo to release the biologically active organic acid from the N-alkyl substituted cyclic lactam, the rate of acid deposition controlled by the rate of hydrolysis.

* * * * *